(12) United States Patent
Inoue et al.

(10) Patent No.: US 10,429,290 B2
(45) Date of Patent: Oct. 1, 2019

(54) PARTICULATE MEASUREMENT APPARATUS AND PARTICULATE MEASUREMENT SYSTEM

(71) Applicant: NGK SPARK PLUG CO., LTD., Nagoya-shi, Aichi (JP)

(72) Inventors: Yoshinori Inoue, Nagoya (JP); Kaoru Hisada, Obu (JP); Yuichi Goto, Konan (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 184 days.

(21) Appl. No.: 15/717,189

(22) Filed: Sep. 27, 2017

(65) Prior Publication Data
US 2018/0088018 A1    Mar. 29, 2018

(30) Foreign Application Priority Data
Sep. 29, 2016 (JP) ................................. 2016-191373

(51) Int. Cl.
*G01N 15/06* (2006.01)
*G01N 27/68* (2006.01)
(Continued)

(52) U.S. Cl.
CPC ......... *G01N 15/0656* (2013.01); *G01N 27/68* (2013.01); *F01N 11/00* (2013.01);
(Continued)

(58) Field of Classification Search
CPC ............... G01N 27/68; G01N 15/0656; G01N 2015/0046; F01N 11/00; F01N 2560/05;
(Continued)

(56) References Cited

U.S. PATENT DOCUMENTS 4,531,486 A * 7/1985 Reif .................... G01N 15/0656
123/198 D
7,406,855 B2 * 8/2008 Tikkanen ............... G01N 27/62
73/23.31

(Continued)

FOREIGN PATENT DOCUMENTS

JP     2005024409 A   *  1/2005
JP     2013-195069 A     9/2013
(Continued)

*Primary Examiner* — Jermele M Hollington
*Assistant Examiner* — Sean Curtis
(74) *Attorney, Agent, or Firm* — Sughrue Mion, PLLC

(57) ABSTRACT

In a particulate measurement apparatus (300) of a particulate measurement system (10), a control section (600) provisionally determines in an anomaly determination process at S130 that a corona core wire (202) is in a wire-breakage anomaly state; namely, that the corona core wire (202) is broken, when a corona low-side current C1 is equal to or smaller than a current determination value C1*min,* and increments a wire-breakage anomaly counter CNB at S140. The control section (600) determines that the corona core wire (202) is in the wire-breakage anomaly state at S170 when the count value of the wire-breakage anomaly counter CNB is equal to or greater than a wire-breakage determination threshold Cth; namely, that the result of the determination at S160 is "Yes".

5 Claims, 6 Drawing Sheets

(51) Int. Cl.
  *F02D 41/22*    (2006.01)
  *F02P 9/00*     (2006.01)
  *F01N 11/00*    (2006.01)
  *F02D 41/14*    (2006.01)
  *G01M 15/10*    (2006.01)
  *G01N 15/00*    (2006.01)

(52) U.S. Cl.
  CPC ...... *F01N 2560/05* (2013.01); *F02D 41/1466* (2013.01); *F02D 41/222* (2013.01); *F02P 9/007* (2013.01); *G01M 15/102* (2013.01); *G01N 2015/0046* (2013.01)

(58) Field of Classification Search
  CPC .... F02D 41/1466; F02D 41/222; Y02T 10/40; Y02T 10/47; F02P 9/007
  USPC .......... 73/23.33, 23.31, 28.02; 250/310, 397, 250/374; 96/26; 324/71.1, 71.4, 324/454–456, 464–465
  See application file for complete search history.

(56) References Cited

U.S. PATENT DOCUMENTS

| | | | | |
|---|---|---|---|---|
| 9,053,912   | B2 * | 6/2015  | Kokubo      | H01J 49/022 |
| 9,581,069   | B2 * | 2/2017  | Motomura    | G01N 15/0656 |
| 9,606,038   | B2 * | 3/2017  | Okuda       | G01N 27/62 |
| 9,719,907   | B2 * | 8/2017  | Motomura    | G01N 15/0656 |
| 9,897,528   | B2 * | 2/2018  | Motomura    | G01N 15/0656 |
| 10,048,223  | B2 * | 8/2018  | Hisada      | G01N 27/70 |
| 10,094,756  | B2 * | 10/2018 | Matsuoka    | G01N 15/0606 |
| 10,094,757  | B2 * | 10/2018 | Hisada      | F01N 11/007 |
| 10,101,257  | B2 * | 10/2018 | Yazawa      | G01N 15/0656 |
| 2012/0234172 | A1 * | 9/2012 | Sugiyama    | G01N 1/2252 96/26 |
| 2012/0262182 | A1 * | 10/2012 | Matsuoka   | G01N 15/0656 324/464 |
| 2013/0219990 | A1 * | 8/2013 | Allmendinger | G01N 33/0027 73/23.31 |
| 2014/0239185 | A1 * | 8/2014 | de Oliveira | G01T 1/2935 250/374 |
| 2014/0326873 | A1 * | 11/2014 | Kokubo     | H01J 49/022 250/288 |
| 2014/0352405 | A1 * | 12/2014 | Motomura   | G01N 15/0656 73/23.31 |
| 2015/0020574 | A1 * | 1/2015 | Motomura    | G01N 15/0656 73/23.31 |
| 2015/0102822 | A1 * | 4/2015 | Okuda       | G01N 27/62 324/464 |
| 2015/0114087 | A1 * | 4/2015 | Sugiyama    | G01M 15/102 73/28.01 |
| 2015/0120229 | A1 * | 4/2015 | Sugiyama    | G01N 15/0606 702/85 |
| 2016/0011093 | A1 * | 1/2016 | Matsuoka    | G01N 15/0656 73/23.33 |
| 2016/0139098 | A1 * | 5/2016 | Inoue       | G01N 33/0054 702/189 |
| 2017/0160234 | A1 * | 6/2017 | Suzuki      | G01M 15/102 |
| 2017/0343463 | A1 * | 11/2017 | Minami     | F02D 41/1466 |
| 2018/0088018 | A1 * | 3/2018 | Inoue       | G01N 15/0656 |
| 2018/0088082 | A1 * | 3/2018 | Inoue       | G01N 27/68 |
| 2018/0143107 | A1 * | 5/2018 | Murase      | G01M 15/102 |
| 2018/0164203 | A1 * | 6/2018 | Koerber     | B03C 3/06 |
| 2019/0064112 | A1 * | 2/2019 | Osawa       | G01N 27/626 |
| 2019/0085748 | A1 * | 3/2019 | Sugiyama    | F01N 11/00 |

FOREIGN PATENT DOCUMENTS

| | | | | |
|---|---|---|---|---|
| JP | 2015036647 A | * | 2/2015 | |
| JP | 2018054428 A | * | 4/2018 | ............ G01N 27/68 |
| JP | 2018054475 A | * | 4/2018 | ........ G01N 15/0656 |

* cited by examiner

PARTICULATE MEASUREMENT APPARATUS AND PARTICULATE MEASUREMENT SYSTEM

BACKGROUND OF THE INVENTION

1. Field of the Invention

The present invention relates to a particulate measurement apparatus and a particulate measurement system which measure the amount of particulates such as soot contained in a gas under measurement.

2. Description of the Related Art

Conventionally, a particulate measurement system has been known which measures the amount of particulates (e.g., soot) contained in a gas under measurement (for example, exhaust gas discharged from an internal combustion engine or the like) (see, for example, Patent Document 1).

Such a particulate measurement system includes a particulate sensor which is exposed to the gas under measurement and detects particulates, and a particulate measurement apparatus which is electrically connected to the particulate sensor through a corona cable and which controls the particulate sensor.

The particulate sensor includes an ion generation section, an electrification chamber, and a trapping section. The particulate measurement apparatus includes an isolation transformer for corona discharge, a particulate computation section, and a corona discharge control section. The corona cable includes a corona core wire for electrically connecting the ion generation section and the isolation transformer for corona discharge, and a shield wire for covering the corona core wire in a state in which the shield wire is electrically insulated from the corona core wire.

Using the ions generated at the ion generation section by means of corona discharge, the particulate measurement system electrifies at least a portion of particulates contained in the gas under measurement in the electrification chamber to produce electrified particulates. The particulate measurement system measures the amount of particulates based on a current which flows in accordance with the amount of the electrified particulates discharged to the outside from the particulate sensor.

[Patent Document 1] Japanese Patent Application Laid-Open (kokai) No. 2013-195069

3. Problems to be Solved by the Invention

However, such a particulate measurement system has the following problem. Due to the influence of an applied external force or the manner of handling of the particulate sensor by a user, an anomaly of the electrical connection state (for example, a wire-breakage anomaly of the corona core wire) may occur at the corona cable, the ion generation section, etc., and an expensive apparatus is required to determine such an anomalous state.

Namely, since high voltage is applied to the corona cable and the ion generation section, direct detection of the voltages from the corona cable and the ion generation section requires an expensive detection apparatus which can withstand high voltage. Use of such an expensive detection apparatus results in increased production cost of the particulate measurement apparatus and the particulate measurement system.

SUMMARY OF THE INVENTION

It is therefore an object of the present invention to provide a particulate measurement apparatus and a particulate measurement system which can determine an anomaly of the electrical connection state at the corona cable, the ion generation section, etc., without having to directly detect the voltage at the corona cable or the ion generation section.

The above object has been achieved by providing, in a first aspect of the invention, (1) a particulate measurement apparatus for electrical connection to a particulate sensor for detecting particulates contained in a gas under measurement and which controls the particulate sensor so as to measure the amount of the particulates contained in the gas under measurement. The particulate measurement apparatus comprises an isolation transformer for corona discharge, a signal line, a particulate computation section, a corona discharge control section, and an anomaly determination section.

The particulate sensor includes an ion generation section, an electrification chamber, a trapping section, and a metallic support.

The ion generation section generates ions by means of corona discharge. The electrification chamber is a chamber into which the gas under measurement is introduced and which electrifies the particulates contained in the gas under measurement by mixing with the ions generated by the ion generation section to thereby produce electrified particulates. The trapping section traps the ions generated by the ion generation section but not used for the electrification of the particulates. The metal support supports the ion generation section, the electrification chamber, and the trapping section in a condition in which the metal support is electrically insulated from the ion generation section, the electrification chamber, and the trapping section.

The isolation transformer for corona discharge has a primary coil and a secondary coil and performs voltage conversion. The signal line forms at least a portion of a signal path extending from the trapping section to a line of a secondary-side reference potential which is a reference potential of the secondary coil. The particulate computation section computes the amount of the particulates contained in the gas under measurement based on the current value of compensation current supplied to the signal line in accordance with the amount of the electrified particulates discharged from the particulate sensor. The corona discharge control section controls the amount of electric power supplied to the primary coil, based on a secondary-side current flowing through the signal path, so as to control ion electric power generated at the secondary coil. Notably, the ion electric power is electric power for generating ions at the ion generation section.

The particulate measurement apparatus is electrically connected to the particulate sensor through a corona cable. The corona cable includes a corona core wire, an inner shield wire, and an outer shield wire.

The corona core wire forms at least a portion of a path for supplying electric power from the secondary coil to the ion generation section. The inner shield wire is electrically insulated from the corona core wire and is electrically connected to the trapping section and the signal line. The outer shield wire is electrically insulated from the corona core wire and the inner shield wire and is electrically connected to the metal support and a line of a primary-side reference potential which is a reference potential of the primary coil.

The anomaly determination section determines, based on the secondary-side current, whether or not the corona core wire is in a wire-breakage anomaly state in which the corona core wire is broken.

In such a particulate measurement apparatus, when an anomaly of the electrical connection state (for example, a wire-breakage anomaly of the corona core wire or the like) has occurred at the corona cable, the ion generation section, etc., the supply of electric power from the secondary coil to the ion generation section is not performed properly. In this case, since the ion generation section cannot generate ions properly, the generation of electrified particulates at the electrification chamber cannot be performed properly, and the trapping of ions at the trapping section cannot be performed properly. Therefore, the current flowing from the trapping section to the signal line through the inner shield wire exhibits an anomalous behavior different from that in the case where the electrical connection state is normal. The secondary-side current also exhibits an anomalous behavior different from that in the case where the electrical connection state is normal.

Therefore, the anomaly determination section can determine the anomaly of the electrical connection state at the corona cable, the ion generation section, etc. (the wire-breakage anomaly state of the corona core wire or the like) based on the secondary-side current. Examples of the wire-breakage anomaly state of the corona core wire include a state in which the corona core wire is broken in the middle and electrical conduction becomes impossible, a state in which the connection between the corona core wire and the secondary coil is broken and electrical conduction becomes impossible, and a state in which the connection between the corona core wire and the ion generation section is broken and electrical conduction becomes impossible.

As a result, the particulate measurement apparatus can determine the anomaly of the electrical connection state at the corona cable, the ion generation section, etc., without directly detecting the voltage at the corona cable or the ion generation section.

Notably, the current value of the compensation current supplied to the signal line in accordance with the amount of electrified particulates discharged from the particulate sensor to the outside has a value corresponding to the amount of the electrified particulates and has a value corresponding to the amount of the particulates contained in the gas under measurement. Also, the current value of the compensation current is not limited to a numerical value which directly represents the current value of the compensation current and may be a numerical value which indirectly represents the current value of the compensation current. For example, the current value of the compensation current may be a numerical value represented through use of any of other state quantities which correlate with the current value of the compensation current, for example, a voltage value which correlates with the current value of the compensation current.

In a preferred embodiment (2) of the above-described particulate measurement apparatus (1), the anomaly determination section determines that the corona core wire is in the wire-breakage anomaly state when the secondary-side current is equal to or smaller than a predetermined determination value.

In the case where the corona core wire is in the wire-breakage anomaly state, the ion electric power generated at the secondary coil can be supplied to a region extending from the secondary coil to the breakage point of the corona core wire, but cannot be supplied to a region extending from the breakage point of the corona core wire to the ion generation section. Namely, in the case where the corona core wire is in the wire-breakage anomaly state, no ions are generated at the ion generation section, and movement of ions from the ion generation section to the trapping section does not occur. Therefore, no current flows to the signal line due to ions trapped by the trapping section.

Therefore, it is possible to determine whether or not the corona core wire is in the wire-breakage anomaly state; i.e., the corona core wire is broken, by comparing the secondary-side current and the predetermined determination value, and determining whether or not the secondary-side current is equal to or smaller than the determination value.

In another preferred embodiment (3) of the above-described particulate measurement apparatus (2), the anomaly determination section determines that the corona core wire is in the wire-breakage anomaly state when the state in which the secondary-side current is equal to or smaller than the determination value continues for a predetermined wire-breakage anomaly time or longer.

Namely, in the case where the secondary-side current becomes equal to or smaller than the determination value, the anomaly determination section does not immediately determine that the corona core wire is in the wire-breakage anomaly state. Instead, the anomaly determination section determines whether or not the corona core wire is in the wire-breakage anomaly state based on the result of the determination as to whether or not the state in which the secondary-side current is equal to or smaller than the determination value continues for the wire-breakage anomaly time or longer. Performing the anomaly determination in the above-described manner prevents the anomaly determination section from immediately making an erroneous determination that the corona core wire is in the wire-breakage anomaly state when the secondary-side current temporarily becomes equal to or smaller than the determination value due to the influence of noise or the like.

Therefore, the particulate measurement apparatus can decrease the frequency of false determinations due to the influence of noise or like, and thus can improve the determination accuracy in determining the wire-breakage anomaly state of the corona core wire.

In yet another preferred embodiment (4), the particulate measurement apparatus of any of (1) to (3) above further comprises an informing section which informs that the corona core wire is in the wire-breakage anomaly state in the case where the anomaly determination section determines that the corona core wire is in the wire-breakage anomaly state.

Since the informing section is provided so as to inform the wire-breakage anomaly state of the corona core wire, it is possible to prompt a user of the particulate measurement apparatus to check the connection state of the corona cable or to exchange the corona cable.

As a result, the particulate measurement apparatus can prevent erroneous particulate measurements in a situation in which the corona core wire is in the wire-breakage anomaly state, to thereby prevent lowering the measurement performance of the particulate sensor.

In a second aspect (5), the invention provides a particulate measurement system of another aspect of the present invention comprises a particulate sensor for detecting particulates contained in a gas under measurement; and the above-described particulate measurement apparatus of any of (1) to (4) above which is electrically connected to the particulate sensor through the corona cable and which controls the particulate sensor so as to measure the amount of the particulates contained in the gas under measurement.

The particulate measurement system, which is configured by connecting the particulate sensor to the above-described particulate measurement apparatus through the corona cable, can determine the anomaly of the electrical connection state at the corona cable, the ion generation section, etc., without directly detecting the voltage at the corona cable or the ion generation section.

EFFECT OF THE INVENTION

The particulate measurement apparatus and the particulate measurement system of the present invention can determine an anomaly of the electrical connection state at the corona cable, the ion generation section, etc., without directly detecting the voltage at the corona cable or the ion generation section.

BRIEF DESCRIPTION OF THE DRAWINGS

FIGS. 1A and 1B are explanatory views describing the overall configuration of a particulate measurement system, wherein FIG. 1A is an explanatory view exemplifying a general configuration of a vehicle on which the particulate measurement system is mounted, and FIG. 1B is an explanatory view exemplifying a general configuration of the particulate measurement system attached to the vehicle.

DESCRIPTION OF REFERENCE NUMERALS

Figure 1A:
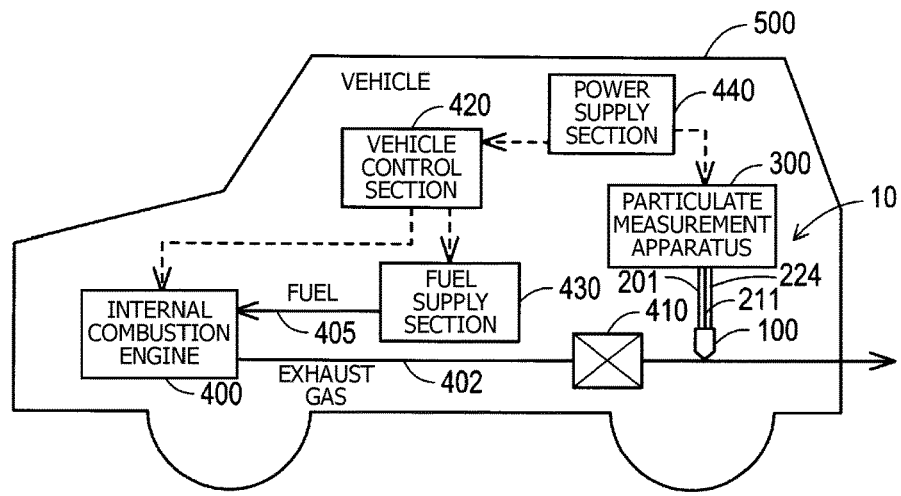

Reference numerals used to identify various features in the drawings include the following.

10: particulate measurement system, 100: particulate sensor, 110: ion generation section, 111: ion generation chamber, 112: first electrode, 120: exhaust gas electrification section, 121: electrification chamber, 130: ion trapping section, 132: second electrode, 140: metallic support, 201: corona cable, 202: corona core wire, 203: corona outer conductor, 204: corona inner conductor, 205: corona cable connector, 211: auxiliary cable, 212: auxiliary core wire, 213: auxiliary outer conductor, 214: auxiliary inner conductor, 215: auxiliary cable connector, 233: first ion current path, 235: auxiliary current path, 236: second reference path, 237: second ion current path, 300: particulate measurement apparatus, 600: control section, 700: electric circuit section, 710: power supply circuit, 710a: first power supply circuit, 710b: second power supply circuit, 711a: first discharge voltage control circuit, 711b: second discharge voltage control circuit, 712a: first transformer drive circuit, 712b: second transformer drive circuit, 720: isolation transformer, 720a: first isolation transformer, 720b: second isolation transformer, 730: corona current measurement circuit, 740: ion current measurement circuit, 751: first rectification circuit, 752: second rectification circuit, 800: air supply section, 920: informing section, 930: operation input section, CS: casing, PGL: primary-side ground, SGL: secondary-side ground.

DETAILED DESCRIPTION OF THE PREFERRED EMBODIMENTS

The invention will next be described in greater detail with reference to the drawings. However, the present invention should not be construed as being limited thereto.

1. First Embodiment

[1-1. Overall Configuration]

The configuration of a particulate measurement system according to the present embodiment will be described.

Figure 1B:
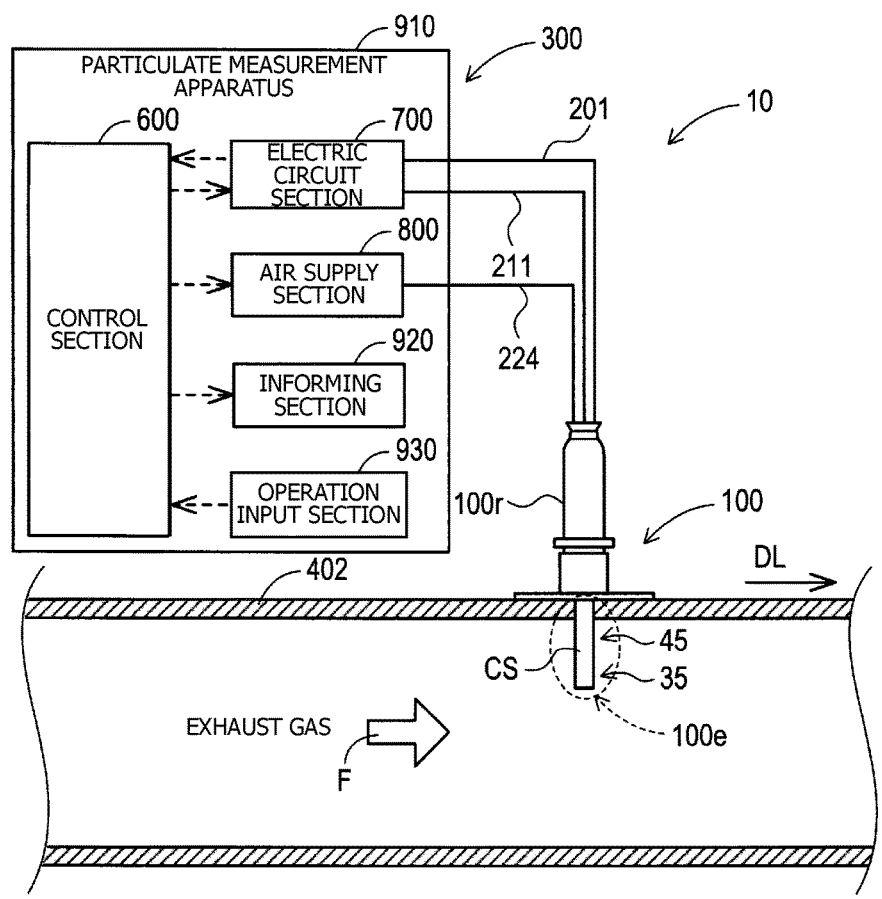

FIGS. 1A and 1B are explanatory views describing the overall configuration of a particulate measurement system 10 according to the first embodiment. FIG. 1A is an explanatory view schematically exemplifying the general configuration of a vehicle 500 on which the particulate measurement system 10 is mounted. FIG. 1B is an explanatory view exemplifying the general configuration of the particulate measurement system 10 attached to the vehicle 500.

The particulate measurement system 10 includes a particulate sensor 100, a corona cable 201, an auxiliary cable 211, an air supply tube 224, and a particulate measurement apparatus 300, and measures the amount of particulates such as soot contained in exhaust gas discharged from an internal combustion engine 400. The internal combustion engine 400, which is a power source of the vehicle 500, is a diesel engine or the like.

The particulate sensor 100 is attached to an exhaust pipe 402 extending from the internal combustion engine 400, and is electrically connected to the particulate measurement apparatus 300 through the corona cable 201 and the auxiliary cable 211. In the present embodiment, the particulate sensor 100 is attached to a portion of the exhaust pipe 402, which portion is located downstream of a filter apparatus 410 (for example, a DPF (diesel particulate filter)). The particulate sensor 100 outputs to the particulate measurement apparatus 300 a signal which correlates with the amount of particulates contained in the exhaust gas.

The particulate measurement apparatus 300 drives the particulate sensor 100 and detects (measures) the amount of particulates contained in the exhaust gas based on the signal input from the particulate sensor 100. The "amount of particulates contained in the exhaust gas" detected by the particulate measurement apparatus 300 may be a value which is proportional to the sum of the surface areas of particulates contained in the exhaust gas or a value which is proportional to the sum of the masses of the particulates. Alternatively, the amount of particulates contained in the exhaust gas may be a value which is proportional to the number of particulates contained in a unit volume of the exhaust gas. The amount of particulates contained in the exhaust gas, which is detected by the particulate measurement apparatus 300, can be used for, for example, analysis of the operation state (combustion state, etc.) of the internal combustion engine 400 and determination of the state of the filter apparatus 410 (deterioration determination, anomaly determination, etc.).

In accordance with signals sent from various portions of the vehicle 500, the vehicle control section 420 controls the combustion state of the internal combustion engine 400, the amount of fuel supplied from a fuel supply section 430 to the internal combustion engine 400 through a fuel pipe 405, etc.

The particulate measurement apparatus 300 and the vehicle control section 420 are electrically connected to a power supply section 440, and electric power is supplied from the power supply section 440 to the particulate measurement apparatus 300 and the vehicle control section 420.

As shown in FIG. 1B, the particulate sensor 100 has a cylindrical distal end portion 100e, and is fixed to the outer surface of the exhaust pipe 402 such that the distal end portion 100e is inserted into the exhaust pipe 402. In the present embodiment, the distal end portion 100e of the particulate sensor 100 is inserted approximately perpendicular to an extension direction DL of the exhaust pipe 402. A casing CS of the distal end portion 100e has an inflow hole 45 and a discharge hole 35 formed on the surface of the casing CS. The inflow hole 45 is used to introduce the exhaust gas into the interior of the casing CS, and the discharge hole 35 is used to discharge the introduced exhaust gas to the outside of the casing CS. A portion of the exhaust gas flowing through the exhaust pipe 402 is introduced into the interior of the casing CS of the distal end portion 100e through the inflow hole 45. Particulates contained in the introduced exhaust gas are electrified by ions (positive ions in the present embodiment) generated by the particulate sensor 100. The exhaust gas containing the electrified particulates is discharged to the outside of the casing CS through the discharge hole 35. The internal structure of the casing CS and the specific structure of the particulate sensor 100 will be described below.

Notably, in the present embodiment, of end portions of the particulate sensor 100 in the longitudinal direction, the end portion where the inflow hole 45 is provided will be referred to as the "distal end portion (side)," and the end portion opposite the forward end portion will be referred to as the "proximal or rear end portion (side)."

The corona cable 201, the auxiliary cable 211, and the air supply tube 224 are attached to a rear end portion 100r of the particulate sensor 100. Each of the corona cable 201, the auxiliary cable 211, and the air supply tube 224 is formed of a flexible member. The corona cable 201 and the auxiliary cable 211 are electrically connected to an electric circuit section 700 of the particulate measurement apparatus 300, and the air supply tube 224 is connected to an air supply section 800 of the particulate measurement apparatus 300.

The particulate measurement apparatus 300 includes a control section 600, the electric circuit section 700, and the air supply section 800, a housing 910, an informing section 920, and an operation input section 930.

The housing 910 has a box-like shape and accommodates the control section 600, the electric circuit section 700, the air supply section 800, the informing section 920, and the operation input section 930. Notably, the housing 910 is configured to allow a user to carry the housing 910. Thus, the user can carry the particulate measurement apparatus 300 to a vehicle to which the particulate sensor 100 is to be attached, and can mount the particulate measurement apparatus 300 onto the vehicle for use.

The informing section 920 includes a display unit disposed on the housing 910 and displays various pieces of information (images, character strings, numerical expressions, etc.) on the display screen of the display unit based on instructions received from the control section 600.

The operation input section 930 includes switches, a touch panel, a voice input device, etc., disposed on the housing 910, and outputs to the control section 600 input operation information for determining an input operation performed by the user through use of the switches, the touch panel, the voice input device, etc.

The control section 600, which includes a microcomputer, executes various types of processes based on input information received from the electric circuit section 700 and the operation input section 930, and controls the electric circuit section 700, the air supply section 800, and the informing section 920. Also, the control section 600 detects (measures) the amount of particulates contained in the exhaust gas from a signal supplied from the electric circuit section 700.

The electric circuit section 700 supplies electric power for driving the particulate sensor 100 through the corona cable 201 and the auxiliary cable 211. A signal which correlates with the amount of particulates contained in the exhaust gas is input from the particulate sensor 100 to the electric circuit section 700 through at least one of the corona cable 201 and the auxiliary cable 211. Using this signal input from the particulate sensor 100, the electric circuit section 700 outputs to the control section 600 a signal corresponding to the amount of particulates contained in the exhaust gas. These signals will be described in detail below.

The air supply section 800 includes a pump (not shown), and supplies high-pressure air to the particulate sensor 100 through the air supply tube 224 based on an instruction received from the control section 600. The high-pressure air supplied from the air supply section 800 is used to drive the particulate sensor 100. Notably, the type of the gas supplied by the air supply section 800 may be other than air.

[1-2. Particulate Sensor]

Figure 2:
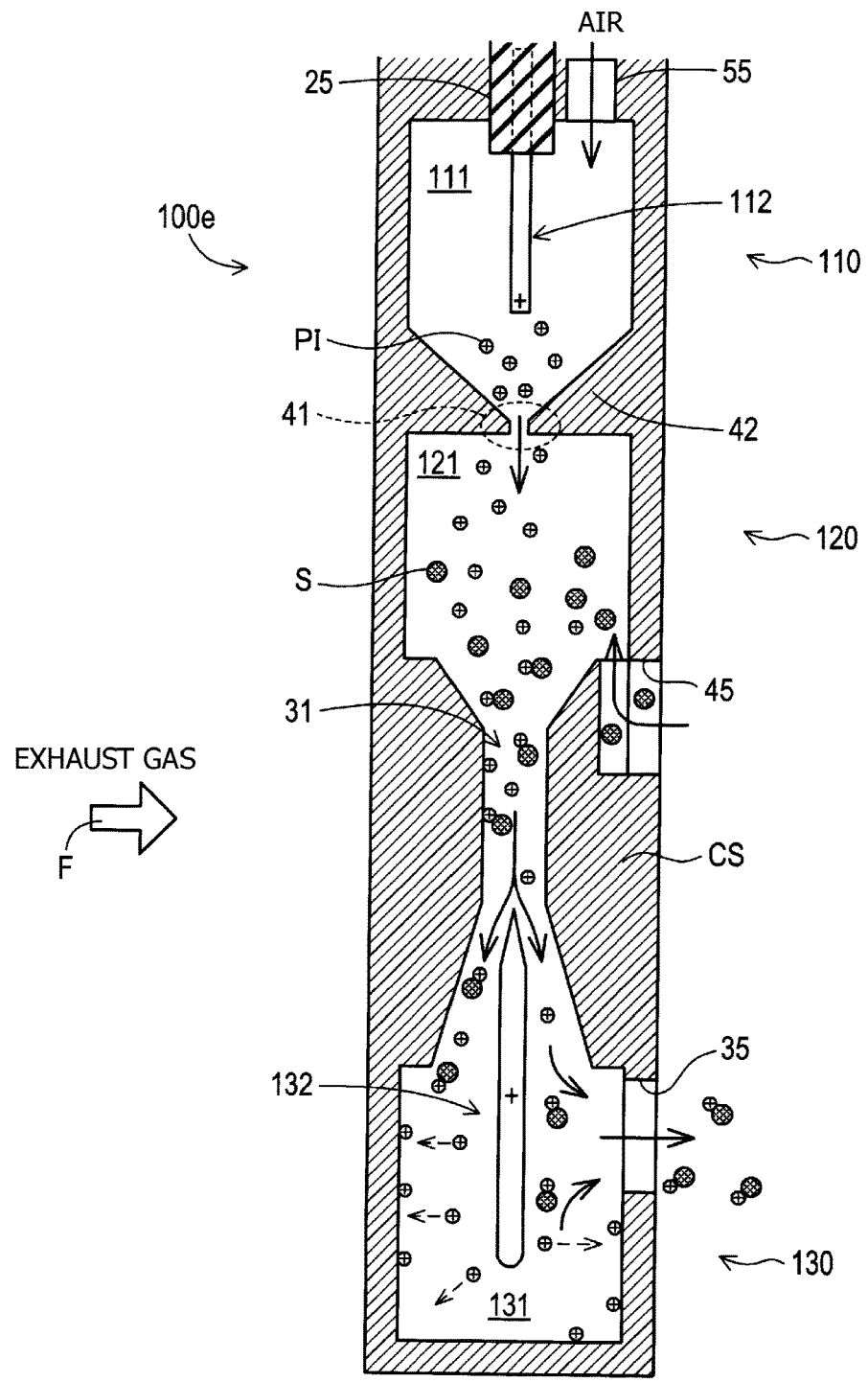
FIG. 2 is an explanatory view schematically showing a general structure of a distal end portion of a particulate sensor.

FIG. 2 is an explanatory view schematically showing the general structure of the distal end portion 100e of the particulate sensor 100.

The distal end portion 100e of the particulate sensor 100 includes an ion generation section 110, an exhaust gas electrification section 120, and an ion trapping section 130. The casing CS has a structure in which the three mechanism sections; i.e., the ion generation section 110, the exhaust gas electrification section 120, and the ion trapping section 130, are arranged in this order from the proximal end side (the upper side in FIG. 2) of the distal end portion 100e toward the distal end side (the lower side in FIG. 2) thereof (along the axial direction of the particulate sensor 100). The casing CS is formed of an electrically conductive material (for example, stainless steel or the like), and is connected to a secondary-side ground SGL (ground (ground line) whose potential serves as a reference potential for the secondary-side circuit in FIG. 3) through at least one of the corona cable 201 (specifically, a corona inner conductor 204 described below) and the auxiliary cable 211 (specifically, an auxiliary inner conductor 214 described below).

The ion generation section 110 is a mechanism section for generating ions (positive ions in the present embodiment) which are supplied to the exhaust gas electrification section 120. The ion generation section 110 includes an ion generation chamber 111 and a first electrode 112. The ion generation chamber 111 is a small space formed inside the casing CS. An air supply hole 55 and a nozzle 41 are provided on the inner circumferential surface of the ion generation chamber 111. The first electrode 112 is attached such that it projects into the ion generation chamber 111. The air supply hole 55 communicates with the air supply tube 224 (FIGS. 1A and 1B), and the high-pressure air supplied from the air supply section 800 (FIG. 1B) is supplied to the ion generation chamber 111 through the air supply hole 55. The nozzle 41 is a very small hole (orifice) provided near the center of a partition wall 42 which separates the ion generation section 110 and the exhaust gas electrification section 120. The nozzle 41 supplies the ions generated in the ion generation chamber 111 to an electrification chamber 121 of the exhaust gas electrification section 120. The first electrode 112 has a rod-like outer shape, and its base end portion is fixed to the casing CS via a ceramic pipe 25 in a state in which a distal end portion of the first electrode 112 is located near the partition wall 42. The first electrode 112 is connected to the electric circuit section 700 (FIG. 1B) through the corona cable 201 (specifically, a corona core wire 202 described below).

The ion generation section 110 is configured such that, by the electric power supplied from the electric circuit section 700, a voltage (e.g., 2 to 3 kV) is applied between the first electrode 112 (positive pole) and the partition wall 42 (negative pole). As a result, the ion generation section 110 produces a corona discharge between a distal end portion of the first electrode 112 and the partition wall 42 to thereby generate positive ions PI. The positive ions PI generated in the ion generation section 110 are jetted into the electrification chamber 121 of the exhaust gas electrification section 120 through the nozzle 41 together with the high-pressure air supplied from the air supply section 800 (FIG. 1B). The jetting speed of air jetted from the nozzle 41 may be set to a speed near the speed of sound.

The exhaust gas electrification section 120 is a section for electrifying the particulates contained in the exhaust gas by positive ions PI, and includes the electrification chamber 121. The electrification chamber 121 is a small space located adjacent to the ion generation chamber 111, and communicates with the ion generation chamber 111 through the nozzle 41. Also, the electrification chamber 121 communicates with the outside of the casing CS through the inflow hole 45, and communicates with a trapping chamber 131 of the ion trapping section 130 through a gas flow passage 31. The electrification chamber 121 is configured such that, when air containing the positive ions PI is jetted from the nozzle 41, a negative pressure is created in the electrification chamber 121, and the exhaust gas located outside the casing CS flows into the electrification chamber 121 through the inflow hole 45. Therefore, the air jetted from the nozzle 41 and containing the positive ions PI and the exhaust gas flowing inward through the inflow hole 45 are mixed together within the electrification chamber 121. At that time, at least a portion of the soot S (particulates) contained in the exhaust gas flowed inward through the inflow hole 45 is electrified by the positive ions PI supplied from the nozzle 41, whereby electrified particulates are produced. The air containing the electrified soot S (electrified particulates) and the positive ions PI not used for the electrification is supplied to the trapping chamber 131 of the ion trapping section 130 through the gas flow passage 31.

The ion trapping section 130 is a section for trapping ions not used for the electrification of the soot S (particulates), and includes the trapping chamber 131 and a second electrode 132. The trapping chamber 131 is a small space located adjacent to the electrification chamber 121, and communicates with the electrification chamber 121 through the gas flow passage 31. Also, the trapping chamber 131 communicates with the outside of the casing CS through the discharge hole 35. The second electrode 132 has a generally rod-like outer shape and is fixed to the casing CS such that its longitudinal direction coincides with the flow direction of air flowing through the gas flow passage 31 (the extending direction of the casing CS). The second electrode 132 is connected to the electric circuit section 700 (FIG. 1B) through the auxiliary cable 211 (specifically, an auxiliary core wire 212 described below). The second electrode 132 is electrically insulated from the casing CS.

A voltage of about 100 V is applied to the second electrode 132, whereby it functions as an auxiliary electrode for assisting the trapping of positive ions not used for the electrification of the soot S. Specifically, by the electric power supplied from the electric circuit section 700, a voltage is applied to the ion trapping section 130 such that the second electrode 132 serves as a positive pole, and the casing CS constituting the electrification chamber 121 and the trapping chamber 131 serves as a negative pole. As a result, the positive ions PI not used for the electrification of soot S receive a repulsive force from the second electrode 132, whereby their advancing directions deviate to directions away from the second electrode 132. The positive ions PI whose advancing directions have been deviated are trapped by the inner circumferential walls of the trapping chamber 131 and the gas flow passage 31 which function as a negative pole. Meanwhile, the soot S (electrified particulates) to which positive ions PI have adhered also receives the repulsive force from the second electrode 132 as in the case of the positive ions PI themselves. However, since the soot S is larger in mass than the positive ions PI, the influence of the repulsive force on the advancing directions is smaller as compared with the case of the positive ions PI themselves. Therefore, the electrified soot S (electrified particulates) is discharged to the outside of the casing CS through the discharge hole 35 as a result of the flow of the exhaust gas.

Notably, a method of calculating the amount of soot S contained in the exhaust gas from the signal output of the particulate sensor 100 described below.

Figure 3:
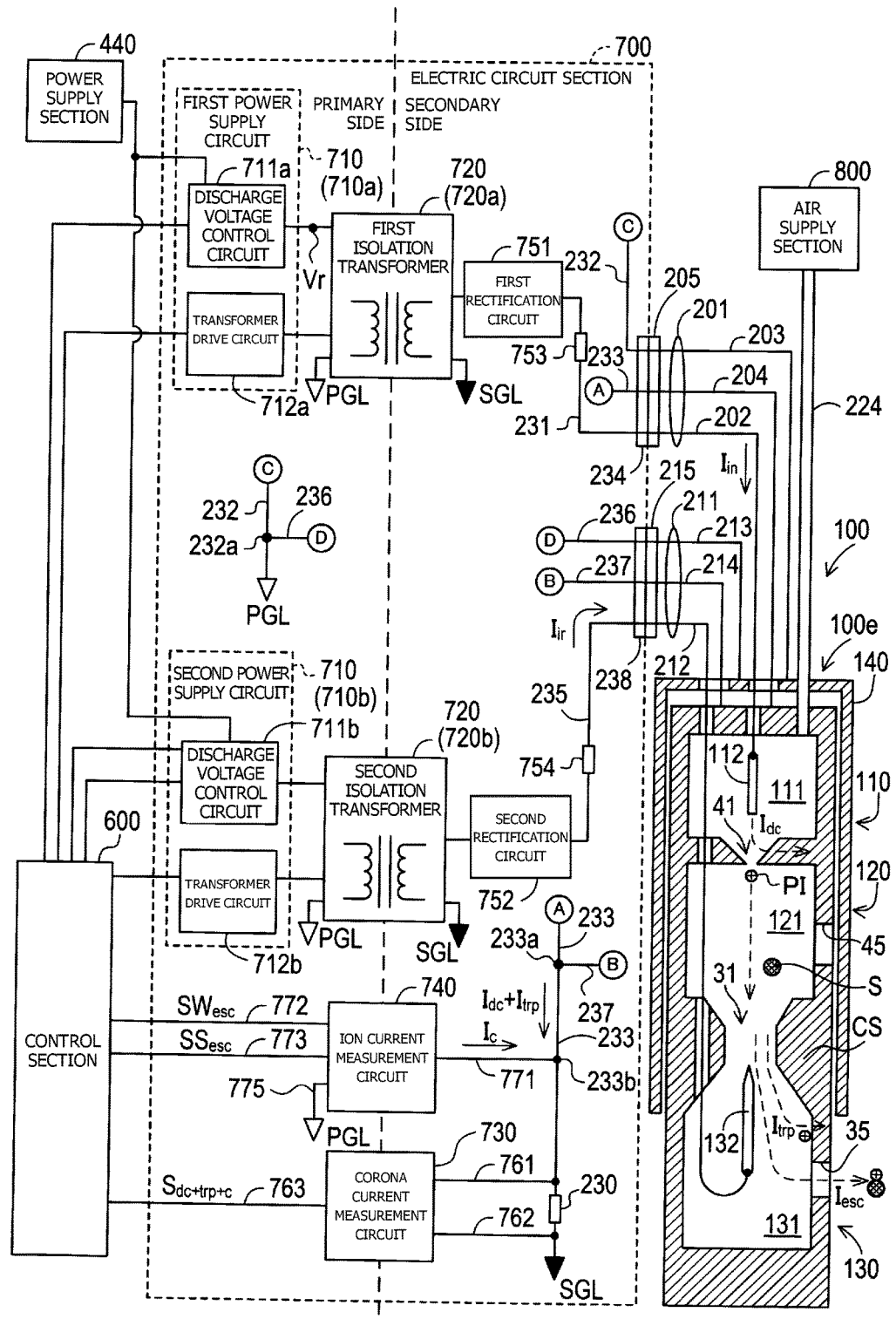
FIG. 3 is an explanatory view showing general electrical configurations of the particulate sensor and an electric circuit section.

FIG. 3 is an explanatory view sowing the electrical configuration of the particulate sensor 100 and the electric circuit section 700.

The particulate sensor 100 has a metallic support 140 which is formed of an electrically conductive material (for example, stainless steel or the like) and which supports the casing CS in a state in which the metallic support 140 is electrically insulated from the casing CS.

The metallic support 140 has a fixing portion (for example, a screw groove or the like) for attachment to the exhaust gas pipe 402 (see FIG. 1B). As a result of being fixed to the exhaust gas pipe 402, the metallic support 140 is electrically connected to the exhaust gas pipe 402 and is connected to a primary-side ground PGL (ground (ground line) whose potential serves as a reference potential for the primary-side circuit).

The corona cable 201 is a so-called triaxial cable and includes the corona core wire 202, a corona outer conductor 203, a corona inner conductor 204, and a corona cable connector 205.

The corona core wire 202 is provided as a center conductor formed of an electrically conductive material (for example, copper or the like). The corona core wire 202 is electrically connected to the first electrode 112 of the particulate sensor 100. The corona inner conductor 204 is a tubular braided wire located on the radially outer side of the corona core wire 202 and electrically insulated from the corona core wire 202, and is formed by braiding thin wires of electrical conductive material (for example, copper or the like). The corona inner conductor 204 is electrically connected to the casing CS of the particulate sensor 100. The corona outer conductor 203 is a tubular braided wire located on the radially outer side of the corona inner conductor 204 and electrically insulated from the corona inner conductor 204, and is formed by braiding thin wires of electrical conductive material (for example, copper or the like). The corona outer conductor 203 is electrically connected to the metallic support 140 of the particulate sensor 100. The corona cable connector 205 is provided at the ends of the corona core wire 202, the corona outer conductor 203, and the corona inner conductor 204.

The auxiliary cable 211 is a so-called triaxial cable and includes an auxiliary core wire 212, an auxiliary outer conductor 213, an auxiliary inner conductor 214, and an auxiliary cable connector 215.

The auxiliary core wire 212 is provided as a center conductor formed of an electrically conductive material (for example, copper or the like). The auxiliary core wire 212 is electrically connected to the second electrode 132 of the particulate sensor 100. The auxiliary inner conductor 214 is a tubular braided wire located on the radially outer side of the auxiliary core wire 212 and electrically insulated from the auxiliary core wire 212, and is formed by braiding thin wires of electrical conductive material (for example, copper or the like). The auxiliary inner conductor 214 is electrically connected to the casing CS of the particulate sensor 100. The auxiliary outer conductor 213 is a tubular braided wire located on the radially outer side of the auxiliary inner conductor 214 and electrically insulated from the auxiliary inner conductor 214, and is formed by braiding thin wires of electrical conductive material (for example, copper or the like). The auxiliary outer conductor 213 is electrically connected to the metallic support 140 of the particulate sensor 100. The auxiliary cable connector 215 is provided at the ends of the auxiliary core wire 212, the auxiliary outer conductor 213, and the auxiliary inner conductor 214.

[1-3. Electric Circuit Section]

As shown in FIG. 3, the electric circuit section 700 includes a power supply circuit 710, an isolation transformer 720, a corona current measurement circuit 730, an ion current measurement circuit 740, a first rectification circuit 751, and a second rectification circuit 752.

Also, the electric circuit section 700 includes a corona current path 231, a first reference path 232, a first ion current path 233, a corona connector 234, an auxiliary current path 235, a second reference path 236, a second ion current path 237, and an auxiliary connector 238.

The corona current path 231 is a current path extending from the corona connector 234 to the first rectification circuit 751. A short protection resistor 753 is provided in the corona current path 231. The first reference path 232 is a current path extending from the corona connector 234 to the primary-side ground PGL. The first ion current path 233 is a current path extending from the corona connector 234 to the secondary-side ground SGL. The corona connector 234 is configured to be connectable with the corona cable connector 205.

When the corona cable connector 205 and the corona connector 234 are connected to each other, the corona core wire 202 is electrically connected to the corona current path 231, the corona outer conductor 203 is electrically connected to the first reference path 232, and the corona inner conductor 204 is electrically connected to the first ion current path 233.

The auxiliary current path 235 is a current path extending from the auxiliary connector 238 to the second rectification circuit 752, and an auxiliary electrode current $I_{in}$ flows through the current path. A short protection resistor 754 is provided in the auxiliary current path 235. The second reference path 236 is a current path extending from the auxiliary connector 238 to a connection point 232a of the first reference path 232 and is electrically connected to the primary-side ground PGL through the first reference path 232. The second ion current path 237 is a current path extending from the auxiliary connector 238 to a connection point 233a of the first ion current path 233 and is electrically connected to the secondary-side ground SGL through the first ion current path 233. The auxiliary connector 238 is configured to be connectable with the auxiliary cable connector 215.

When the auxiliary cable connector 215 and the auxiliary connector 238 are connected to each other, the auxiliary core wire 212 is electrically connected to the auxiliary current path 235, the auxiliary outer conductor 213 is electrically connected to the second reference path 236, and the auxiliary inner conductor 214 is electrically connected to the second ion current path 237.

The power supply circuit 710 includes a first power supply circuit 710a and a second power supply circuit 710b. The isolation transformer 720 includes a first isolation transformer 720a and a second isolation transformer 720b.

The first power supply circuit 710a supplies to the first isolation transformer 720a the electric power supplied from the power supply section 440, and drives the first isolation transformer 720a. The first power supply circuit 710a includes a first discharge voltage control circuit 711a and a first transformer drive circuit 712a. The first discharge voltage control circuit 711a is configured such that it can arbitrarily change the voltage value of the electric power supplied to the first isolation transformer 720a under the control by the control section 600. In the present embodiment, the control section 600 controls the voltage value of the electric power supplied to the first isolation transformer 720a such that the current value of input current $I_{in}$ supplied to the first electrode 112 of the particulate sensor 100 through the corona cable 201 (specifically, the corona core wire 202) becomes equal to a target current value $I_{ta}$ (e.g., 5 μA) set in advance. The method of this control by the control section 600 will be described below. As a result, the amount of positive ions PI generated by the corona discharge in the ion generation section 110 can be made constant.

The first transformer drive circuit 712a includes a switch which can switch the flow direction of current flowing through the primary coil of the first isolation transformer 720a. The first transformer drive circuit 712a drives the first isolation transformer 720a by the switching operation of the switch. In the present embodiment, the circuit type of the first isolation transformer 720a is a push-pull type. However, the circuit type of the first isolation transformer 720a is not limited thereto and may be, for example, a half-bridge type or a full-bridge type.

The first isolation transformer 720a performs voltage conversion for the electric power supplied from the first power supply circuit 710a, and supplies the voltage-converted electric power to the first rectification circuit 751 on the secondary side. The first isolation transformer 720a of the present embodiment is configured such that the primary coil and the secondary coil are not in physical contact with each other but are magnetically coupled with each other. A circuit on the primary side of the first isolation transformer 720a includes the control section 600 and the power supply section 440 as well as the first power supply circuit 710a. A circuit on the secondary side of the first isolation transformer 720a includes the particulate sensor 100 and the first rectification circuit 751.

The second power supply circuit 710b supplies to the second isolation transformer 720b the electric power supplied from the power supply section 440, and drives the second isolation transformer 720b. The second power supply circuit 710b includes a second discharge voltage control circuit 711b and a second transformer drive circuit 712b.

The second discharge voltage control circuit 711b is configured such that it can arbitrarily change the voltage value of the electric power supplied to the second isolation transformer 720b under the control by the control section 600. In the present embodiment, the control section 600 controls the voltage value of the electric power supplied to the second isolation transformer 720b such that the voltage supplied to the second electrode 132 of the particulate sensor 100 through the auxiliary cable 211 (specifically, the auxiliary core wire 212) becomes equal to a target voltage value (e.g., 100 V) set in advance.

The second transformer drive circuit 712b includes a switch which can switch the flow direction of current flowing through the primary coil of the second isolation transformer 720b. The second transformer drive circuit 712b drives the second isolation transformer 720b by the switching operation of the switch. In the present embodiment, the circuit type of the second isolation transformer 720b is a push-pull type. However, the circuit type of the second isolation transformer 720b is not limited thereto and may be, for example, a half-bridge type or a full-bridge type.

The second isolation transformer 720b performs voltage conversion for the electric power supplied from the second power supply circuit 710b, and supplies the voltage-converted electric power to the second rectification circuit 752 on the secondary side. The second isolation transformer 720b of the present embodiment is configured such that the primary coil and the secondary coil are not in physical contact with each other but are magnetically coupled with each other. A circuit on the primary side of the second isolation transformer 720b includes the control section 600 and the power supply section 440 as well as the second power supply circuit 710b. A circuit on the secondary side of the second isolation transformer 720b includes the particulate sensor 100 and the second rectification circuit 752.

The corona current measurement circuit 730 and the ion current measurement circuit 740 are circuits provided between the circuit on the primary side of the isolation transformer 720 (the first isolation transformer 720a and the second isolation transformer 720b) and the circuit on the secondary side of the isolation transformer 720 (the first isolation transformer 720a and the second isolation transformer 720b), and are electrically connected to the primary-side and secondary-side circuits, respectively. As described below, the corona current measurement circuit 730 is configured such that a circuit portion electrically connected to the circuit on the primary side of the isolation transformer 720 (the first isolation transformer 720a and the second isolation transformer 720b) is physically insulated from a circuit portion electrically connected to the circuit on the secondary side of the isolation transformer 720 (the first isolation transformer 720a and the second isolation transformer 720b). Notably, as described above, the ground (ground line) which provides the reference potential of the primary-side circuit is also referred to as a "primary-side ground PGL," and the ground which provides the reference potential of the secondary-side circuit is also referred to as a "secondary-side ground SGL."

Ends of the primary coils of the isolation transformer 720 (the first isolation transformer 720a and the second isolation transformer 720b) are connected to the primary-side ground PGL, and ends of the secondary coils thereof are connected to the secondary-side ground SGL. First ends of the corona internal conductor 204 of the corona cable 201 and the auxiliary internal conductor 214 of the auxiliary cable 211 are connected to the casing CS, and second ends of the corona internal conductor 204 of the corona cable 201 and the auxiliary internal conductor 214 of the auxiliary cable 211 are connected to the secondary-side ground SGL through the first ion current path 233 and the second ion current path 237.

The first rectification circuit 751 is connected to the first electrode 112 through the short protection resistor 753, and supplies the converted electric power to the first electrode 112 through the corona core wire 202 of the corona cable 201. Namely, the voltage supplied from the first rectification circuit 751 becomes mostly a discharge voltage at the first electrode 112, and the current supplied from the first rectification circuit 751 becomes an input current $I_{in}$ input to the first electrode 112. The second rectification circuit 752 is connected to the second electrode 132 through the short protection resistor 754, and applies the converted voltage to the second electrode 132 through the auxiliary core wire 212 of the auxiliary cable 211.

The ion current measurement circuit 740 detects the current value of a current ($I_{esc}$) corresponding to the positive ions PI having flowed out without being trapped by the ion trapping section 130 and supplies to the secondary-side circuit a current (compensation current $I_c$) corresponding to the positive ions PI having flowed out. Namely, the ion current measurement circuit 740 supplies, as the compensation current $I_c$, to the secondary-side circuit, a current corresponding to the amount of the electrified soot S (electrified particulates) discharged from the particulate sensor 100 (the casing CS) to the outside. The ion current measurement circuit 740 is connected to the first ion current path 233 on the secondary side (specifically, a portion of the first ion current path 233 located between the connection point 223a and the shunt resistor 230) through a wiring line 771, and is connected to the control section 600 on the primary side through wiring lines 772 and 773. Also, the ion current measurement circuit 740 is connected to the primary-side ground PGL through the wiring line 775. Through the wiring line 772, the ion current measurement circuit 740 outputs to the control section 600 a signal $SW_{esc}$ having a current value corresponding to the amount of positive ions PI having flowed out without being trapped by the ion trapping section 130. The ion current measurement circuit 740 also outputs a signal $SS_{esc}$ to the control section 600 through the wiring line 773, the signal $SS_{esc}$ being obtained by amplifying the signal $SW_{esc}$ and serving as a high sensitivity signal.

The corona current measurement circuit 730 is connected to the first ion current path 233 through wiring lines 761 and 762, and is connected to the control section 600 through a wiring line 763. The wiring lines 761 and 762 are connected to the first ion current path 233 such that the shunt resistor 230 provided in the first ion current path 233 is located between the wiring lines 761 and 762. The corona current measurement circuit 730 outputs to the control section 600 a signal $S_{dc+trp+c}$ representing the current value of a secondary-side current ($I_{dc}+I_{trp}+I_c$) flowing from the casing CS toward the secondary-side ground SGL through the first ion current path 233. Here, a "signal representing the current value" is not limited to a signal which directly represents the current value, and may be a signal which indirectly represents the current value. For example, the "signal representing the current value" may be a signal on the basis of which the current value can be specified by applying a computation expression or a map to information obtained from the signal. Notably, since the compensation current $I_c$ supplied (supplemented) from the ion current measurement circuit 740 corresponds to the current corresponding to the positive ions PI (electrified particulates) discharged from the particulate sensor 100 (the casing CS), the current value of the secondary-side current which includes the compensation current $I_c$ and which flows from the casing CS to the secondary-side ground SGL; i.e., the current value of the secondary-side current ($I_{dc}+I_{trp}+I_c$) flowing through the shunt resistor 230, becomes equal to the current value of the input current $I_{in}$.

Using the signal $S_{dc+trp+c}$ input from the corona current measurement circuit 730, the control section 600 controls the first discharge voltage control circuit 711a such that the current value of the input current $I_{in}$ becomes equal to a target current value $I_{ta}$. Namely, the corona current measurement circuit 730 and the control section 600 constitute a constant current circuit for maintaining the current value of the corona current (=the input current $I_{in}$) at a constant level. Since the current value of the corona current correlates with the amount of positive ions PI generated at the ion generation section 110, the amount of positive ions PI generated at the ion generation section 110 is maintained constant by this constant current circuit.

A method will be described by which the ion current measurement circuit 740 detects the current value of the current corresponding to the positive ions PI having flowed out without being trapped by the ion trapping section 130.

Here, the current supplied from the corona core wire 202 of the corona cable 201 to the first electrode 112 is referred to as "input current $I_{in}$"; the current flowing from the first electrode 112 to the casing CS through the partition wall 42 due to corona discharge is referred to as "discharge current $I_{dc}$"; the current corresponding to the charge of the positive ions PI which are some of the positive ions PI generated due to corona discharge, are used for electrification of the soot S, and leak to the outside of the casing CS is referred to as "signal current $I_{esc}$"; and the current corresponding to the charge of the positive ions PI trapped by the casing CS is referred to as "trapped current $I_{trp}$." These four currents satisfy the relation of expression (1) shown below.

$$I_{in}=I_{dc}+I_{trp}+I_{esc} \tag{1}$$

Here, the signal current $I_{esc}$ is a signal which has a current value corresponding to the current output from the ion current measurement circuit 740 which is a current (compensation current $I_c$) corresponding to the positive ions PI which have flowed out. Therefore, by detecting the compensation current $I_c$, the ion current measurement circuit 740 can detect the current value of the current ($I_{esc}$) corresponding to the positive ions PI having flowed out without being trapped by the ion trapping section 130.

Notably, the compensation current $I_c$ is also a signal representing the difference in potential between the primary-side ground PGL and the secondary-side ground SGL. Also, the compensation current $I_c$ is a current representing a current value equivalent to the signal current $I_{esc}$. In consideration of expression (1), the compensation current $I_c$ has a current value corresponding to the difference between ($=I_{in}-I_{dc}-I_{trp}$) obtained by subtracting the current ($=I_{trp}$) corresponding to the amount of ions trapped by the ion trapping section 130 from the current ($=I_{in}-I_{dc}$) corresponding to the amount of ions generated at the ion generation section 110. Namely, the compensation current $I_c$ is a state quantity which correlates with the difference obtained by subtracting the amount of ions trapped by the ion trapping section 130 from the amount of ions generated at the ion generation section 110 by the ion electric power.

[1-4. Ion Current Measurement Circuit]

Figure 4:
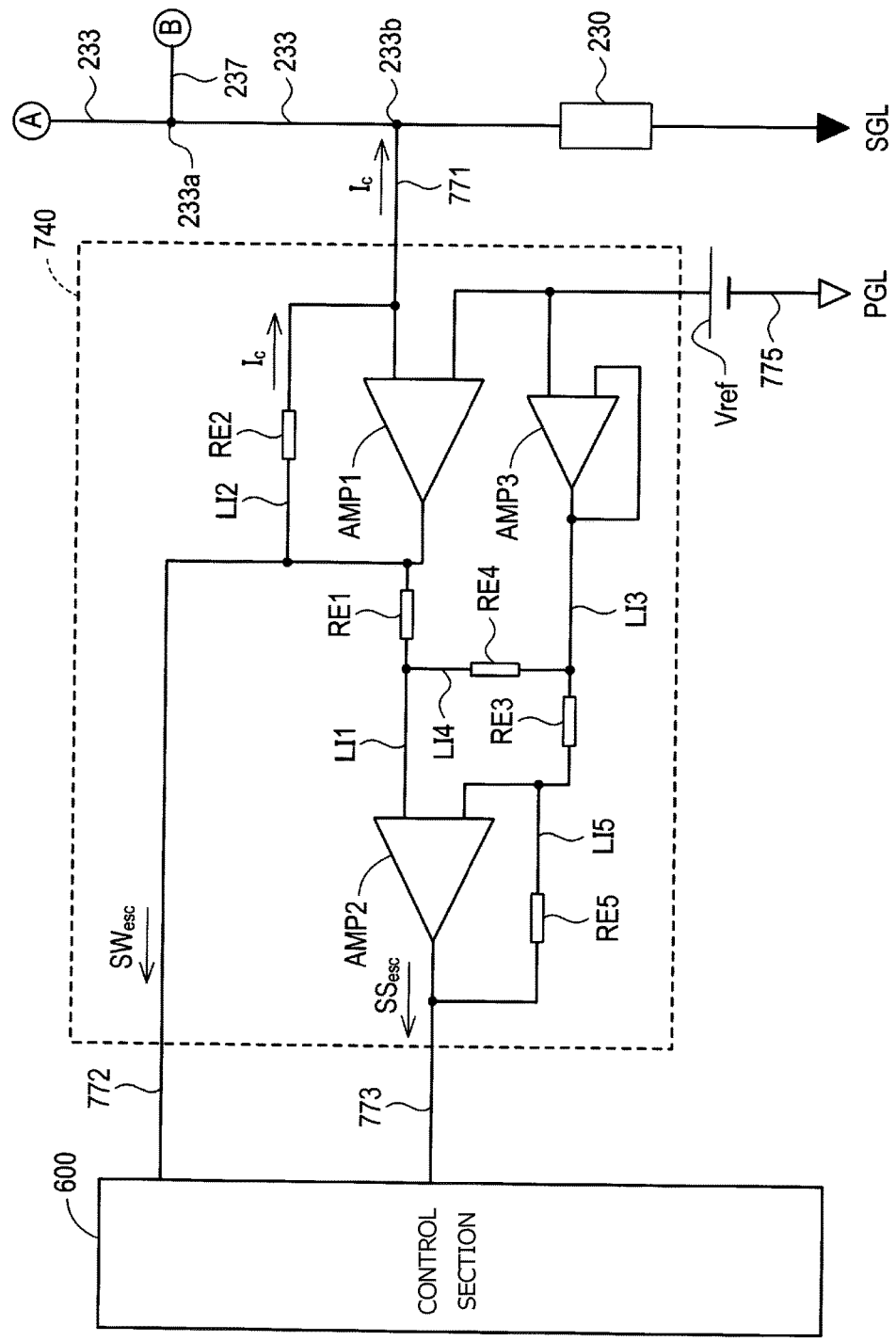
FIG. 4 is an explanatory view exemplifying a general configuration of an ion current measurement circuit.

FIG. 4 is an explanatory view exemplifying the general configuration of the ion current measurement circuit 740.

The ion current measurement circuit 740 includes a first operational amplifier AMP1, a second operational amplifier AMP2, a third operational amplifier AMP3, and resistors RE1 to RE5 having known resistances.

One input terminal of the first operational amplifier AMP1 is connected to the secondary-side ground SGL through the wiring line 771 and the first ion current path 233 (including the shunt resistor 230), and the other input terminal of the first operational amplifier AMP1 is connected to the primary-side ground PGL through the wiring line 775. The output terminal of the first operational amplifier AMP1 is connected to the control section 600 through the wiring line 772. Notably, a power source Vref for providing a constant reference voltage (for example, 0.5 V) in relation to the primary-side ground PGL is connected to the other input terminal of the first operational amplifier AMP1. By inputting the reference voltage to the first operational amplifier AMP1, it is possible to cause the potential difference between the two input terminals of the first operational amplifier AMP1 to approach a potential difference range within which an error (error due to bias current, offset voltage, etc.) is hardly produced. Also, the output terminal of the first operational amplifier AMP1 is connected to one input terminal of the second operational amplifier AMP2 through a portion of the wiring line 772 and a wiring line LI1, and is connected to the wiring line 771 through a portion of the wiring line 772 and a wiring line LI2. The resistor RE1 is provided in the wiring line LI1, and the resistor RE2 is provided in the wiring line LI2.

One input terminal of the second operational amplifier AMP2 is connected to the first operational amplifier AMP1 through a portion of the wiring line LI1 and the wiring line 772, and the other input terminal of the second operational amplifier AMP2 is connected to the primary-side ground PGL through a wiring line LI3 and the wiring line 775. The resistor RE3 and the third operational amplifier AMP3 are provided in the wiring line LI3. A wiring line LI4 is connected to a node between the resistor RE3 and the third operational amplifier AMP3. The wiring line LI3 is connected to the wiring line LI1 through the wiring line LI4 in which the resistor RE4 is provided. The third operational amplifier AMP3 is configured to function as a voltage follower which suppresses voltage change due to current change on the output side. The output terminal of the second operational amplifier AMP2 is connected to the control section 600 through the wiring line 773, and is connected to the wiring line LI3 through the wiring line 773 and a wiring line LI5. The resistor RE5 is provided in the wiring line LI5.

When a difference is produced between the reference potential of the secondary-side ground SGL and the reference potential of the primary-side ground PGL as a result of generation of the signal current $I_{esc}$, the first operational amplifier AMP1 outputs a voltage corresponding to this difference. Since the voltage output from the first operational amplifier AMP1 correlates with the current value of the signal current $I_{esc}$, this voltage value is output to the control section 600 through the wiring line 772 as a signal $SW_{esc}$ representing the current value of the signal current $I_{esc}$.

Also, the voltage output from the first operational amplifier AMP1 produces the compensation current $I_c$, which is supplied from the wiring line LI2 to the wiring line 771 through the resistor RE2. As described above, the current value of the compensation current $I_c$ is equal to the current value of the signal current $I_{esc}$. Therefore, as a result of supply of the compensation current $I_c$ to the wiring line 771 which constitutes the secondary-side circuit, the difference between the reference potential of the secondary-side ground SGL and the reference potential of the primary-side ground PGL is compensated.

The second operational amplifier AMP2 amplifies the signal $SW_{esc}$ input from the first operational amplifier AMP1, and outputs to the control section 600 the signal $SS_{esc}$ obtained as a result of the amplification. Since the second operational amplifier AMP2 is configured to function as a differential amplification circuit, the second operational amplifier AMP2 outputs a voltage corresponding to the difference between the voltage input to one input terminal as the signal $SW_{esc}$ and the reference potential of the primary-side ground PGL input to the other input terminal. Namely, the second operational amplifier AMP2 outputs a voltage to the control section 600 as the signal $SS_{esc}$, the voltage being obtained by amplifying the voltage of the input signal $SW_{esc}$ at a predetermined amplification factor (e.g., $10^3$ times).

The control section 600 detects the amount of soot S contained in the exhaust gas through use of the signal $SW_{esc}$ (low sensitivity signal) and the signal $SS_{esc}$ (high sensitivity signal) input from the ion current measurement circuit 740. No particular limitation is imposed on the method of detecting the amount of soot S contained in the exhaust gas using these signals representing the current value of the signal current $I_{esc}$. For example, in the case where the control section 600 stores a map or a relational expression showing the relation between the voltage value of the signal and the amount of soot S contained in the exhaust gas, the control section 600 can calculate the amount of soot S contained in the exhaust gas using the map or the relational expression.

The control section 600 of the present embodiment obtains each of the voltage values, which are analog signals input thereto as the signals $SS_{esc}$ and $SW_{esc}$, as a digital value of a predetermined resolution (for example, 8 bits). Also, the control section 600 is configured such that the size of the voltage readable range (the range of the full scale) becomes the same for the signals $SS_{esc}$ and $SW_{esc}$ input thereto.

The signal $SS_{esc}$ (high sensitivity signal) has a higher sensitivity (resolution) for the current value of the signal current $I_{esc}$ as compared with the signal $SW_{esc}$ (low sensitivity signal). For example, whereas a voltage level of the signal $SW_{esc}$ of 1 V corresponds to a magnitude of the signal current $I_{esc}$ of 1 nA, a voltage level of the signal $SS_{esc}$ of 1 V corresponds to a magnitude of the signal current $I_{esc}$ of 1 pA. Meanwhile, the control section 600 has the same voltage resolution (the minimum recognizable potential difference) (for example, 0.02 V) for both the signals $SS_{esc}$ and $SW_{esc}$. Accordingly, the current value of the signal current $I_{esc}$ corresponding to the voltage resolution of the control section 600 is small for the case of the signal $SS_{esc}$ (e.g., 0.02 pA) and is large for the case of the signal $SW_{esc}$ (e.g., 0.02 nA). In other words, the control section 600 can detect a smaller change in the signal current $I_{esc}$ from signal $SS_{esc}$, as compared with the signal $SW_{esc}$.

Therefore, the amount of soot S contained in the exhaust gas obtained from the signal $SS_{esc}$ is smaller in the minimum recognizable unit and is higher in accuracy than the amount of soot S contained in the exhaust gas obtained from the signal $SW_{esc}$. Meanwhile, the readable voltage range (e.g., 0 to 5 V) of the control section 600 is set to cover the entire voltage range of the signal $SW_{esc}$. Therefore, a range in which the amount of soot S contained in the exhaust gas can be measured through use of the signal $SW_{esc}$ is wider than a range in which the amount of soot S contained in the exhaust gas can be measured through use of the signal $SS_{esc}$. If the amount of soot S contained in the exhaust gas falls within a range corresponding to the entire voltage range of the signal $SW_{esc}$, the amount of soot S can be measured within the entire range.

As can be understood from the above, when the voltage value of the signal $SS_{esc}$ falls within the readable voltage range, the control section 600 can accurately measure the amount of soot S contained in the exhaust gas through use of the signal $SS_{esc}$, and when the voltage value of the signal $SS_{esc}$ falls outside the readable voltage range, the control section 600 can measure the amount of soot S contained in the exhaust gas through use of the signal $SW_{esc}$ which allows measurement within a wider range.

[1-5. Corona Current Measurement Circuit]

Figure 5:
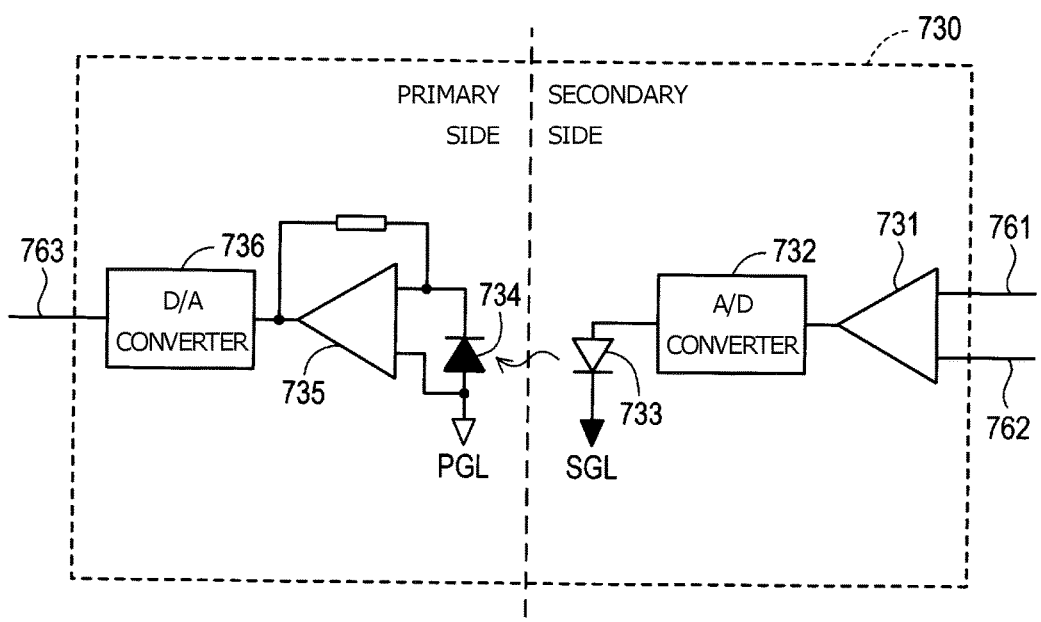
FIG. 5 is an explanatory view exemplifying a general configuration of a corona current measurement circuit.

FIG. 5 is an explanatory view exemplifying the general configuration of the corona current measurement circuit 730.

The corona current measurement circuit 730 is configured as a so-called optical-coupling-type isolation amplifier whose input and output sides are isolated from each other. The input side of the corona current measurement circuit 730 belongs to the secondary side of the electric circuit section 700 (FIG. 3), and the output side of the corona current measurement circuit 730 belongs to the primary side of the electric circuit section 700. The corona current measurement circuit 730 includes a secondary-side operational amplifier 731, an A/D converter 732, a light emitting section 733, a light receiving section 734, a primary-side operational amplifier 735, and a D/A converter 736.

The two input terminals of the secondary-side operational amplifier 731 are connected to the wiring line 761 and the wiring line 762, respectively, and the output terminal thereof is connected to the A/D converter 732. The secondary-side operational amplifier 731 amplifies the potential difference between the wiring line 761 and the wiring line 762 and outputs the amplified potential difference to the A/D converter 732. The potential difference between the wiring line 761 and the wiring line 762 is the potential difference between the opposite ends of the shunt resistor 230 (FIG. 3) whose resistance is known, and correlates with the current value of the current flowing through the first ion current path 233 (FIG. 3) (the secondary-side current ($I_{dc}+I_{trp}+I_c$)). Namely, the secondary-side operational amplifier 731 amplifies an analogue voltage signal representing the current value of the current flowing through the first ion current path 233 (FIG. 3) and outputs the amplified analogue voltage signal to the A/D converter 732.

The A/D converter 732, which is connected to the secondary-side operational amplifier 731 and the light emitting section 733, converts the analog signal output from the secondary-side operational amplifier 731 to a digital signal and outputs the digital signal to the light emitting section 733.

The light emitting section 733 includes an LED and is connected to the A/D converter 732 and the secondary-side ground SGL. The light emitting section 733 converts the digital voltage signal output from the A/D converter 732 to an optical signal.

The light receiving section 734 includes a photodiode and is connected to the primary-side operational amplifier 735 and the primary-side ground PGL. The light receiving section 734 converts the optical signal output from the light emitting section 733 to a current signal and outputs the current signal to the primary-side operational amplifier 735. In this manner, the light emitting section 733 and the light receiving section 734 are electrically and physically isolated from each other, and signals are transmitted between the light emitting section 733 and the light receiving section 734 through the mediation of light.

The primary-side operational amplifier 735 is connected to the light receiving section 734 and the D/A converter 736, and includes a current-voltage-conversion circuit. The primary-side operational amplifier 735 converts the current signal output from the light receiving section 734 to a voltage signal and outputs the voltage signal to the D/A converter 736. The D/A converter 736, which is connected to the primary-side operational amplifier 735 and the wiring line 763, converts the digital signal output from the primary-side operational amplifier 735 to an analog signal and outputs the analog signal to the control section 600 (FIG. 3) through the wiring line 763. Since the corona current measurement circuit 730 has the above-described configuration, the corona current measurement circuit 730 can output to the control section 600 on the primary side the signal input from the first ion current path 233 on the secondary side, while maintaining the isolation between the primary side and the secondary side.

[1-6. Processes Executed by Control Section]

The control section 600 includes a microcomputer and executes various types of processes. The control section 600 executes at least a particulate measurement process and an anomaly determination process as the various types of processes.

First, the particulate measurement process will be described briefly.

The particulate measurement process is a process for computing the amount of soot S using the signals $SS_{esc}$ and $SW_{esc}$ from the ion current measurement circuit 740. For example, in the particulate measurement process, an ion current A corresponding to the signal current $I_{esc}$ is computed (measured) through use of the low sensitivity signal $SW_{esc}$ and the high sensitivity signal signals $SS_{esc}$ input from the ion current measurement circuit 740. Subsequently, in the particulate measurement process, the amount of soot S corresponding to the ion current A obtained through the measurement is computed through use of a map showing the relation between the ion current A and the amount of soot S in the exhaust gas or a relational expression representing the relation between the ion current A and the amount of soot S in the exhaust gas. Notably, the map, formulas, etc. may be stored in the storage section (RAM, etc.) of the control section 600 in advance.

After having computed the amount of soot S by the particulate measurement process, the control section 600 outputs to the informing section 920 information regarding the amount of soot S (the amount of particulates) obtained through the computation. As described above, the informing section 920 includes a display unit disposed on the casing 910, and displays the received information on the display unit.

Figure 6:
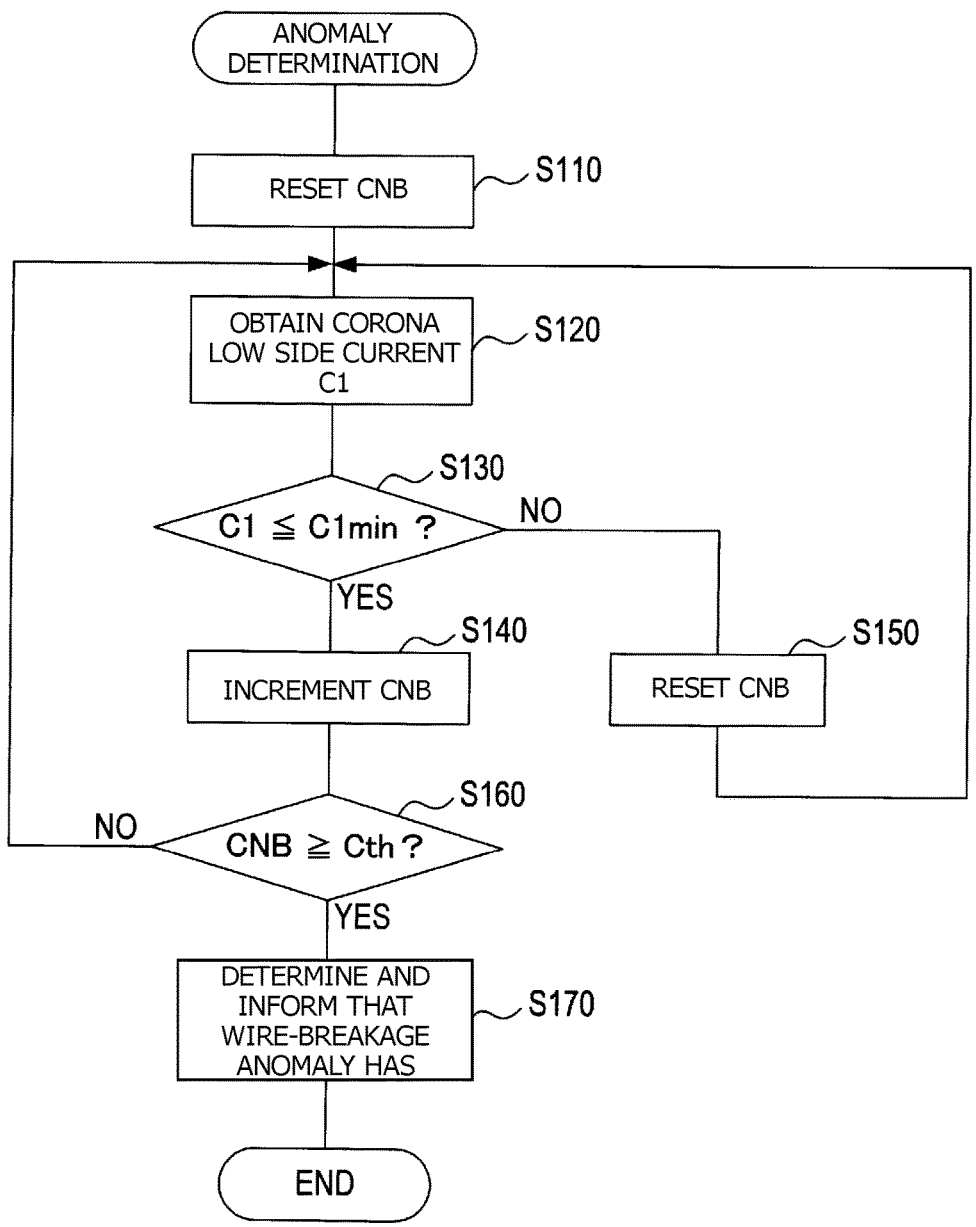
FIG. 6 is a flowchart representing the details of an anomaly determination process.

Next, the anomaly determination process will be described. FIG. 6 is a flowchart showing the details of the anomaly determination process. The anomaly determination process is a process for determining whether or not the corona core wire 202 is in a wire-breakage anomaly state.

Examples of the wire-breakage anomaly state of the corona core wire 202 include a state in which the corona core wire 202 is broken in the middle and electrical conduction becomes impossible, a state in which the connection between the corona core wire 202 and the secondary coil of the first isolation transformer 720*a* is broken and electrical conduction becomes impossible, and a state in which the connection between the corona core wire 202 and the first electrode 112 is broken and electrical conduction becomes impossible.

The anomaly determination process is executed when the control section 600 is started.

When the anomaly determination process is executed, first, in S110 (S stands for "step"), the control section 600 resets a wire-breakage anomaly counter CNB (CNB=0).

The wire-breakage anomaly counter CNB counts the number of times that the wire-breakage anomaly state of the corona core wire 202 occurs.

In S120 subsequent thereto, the control section 600 obtains a corona low side current C1. The corona low side current C1 refers to the current which flows from the casing CS to the secondary-side ground SGL through the first ion current path 233. In the present embodiment, the control section 600 obtains the signal $S_{dc+trp+c}$ which represents the current value of the secondary-side current $(I_{dc}+I_{trp}+I_c)$ flowing through the first ion current path 233 (specifically, the shunt resistor 230), computes the secondary-side current $(I_{dc}+I_{trp}+I_c)$ based on the signal $S_{dc+trp+c}$, and obtains the computation result as the corona low side current C1.

In S130 subsequent to S120, the control section 600 determines whether or not the corona low side current C1 is equal to or smaller than a current determination value C1*min* determined in advance (C1≤C1*min*). When the control section 600 makes an affirmative determination (Yes), the control section 600 proceeds to S140, and when the control section 600 makes a negative determination (No), the control section 600 proceeds to S150. In the present embodiment, the current determination value C1*min* is 2 μA.

Notably, in the case where the wire-breakage anomaly of the corona core wire 202 has occurred, the supply of electric power from the secondary coil of the first isolation transformer 720*a* to the ion generation section 110 is not performed properly. In this case, since the ion generation section 110 cannot generate ions properly, the generation of electrified particulates at the electrification chamber 121 cannot be performed properly, and the trapping of ions at the ion trapping section 130 cannot be performed properly. Therefore, the current which flows from the ion trapping section 130 to the first ion current path 233 through the corona inner conductor 204 exhibits an anomalous behavior different from that in the case where the electrical connection state is normal, and the secondary-side current $(I_{dc}+I_{trp}+I_c)$ flowing through the shunt resistor 230 of the first ion current path 233 also exhibits an anomalous behavior different from that in the case where the electrical connection state is normal.

Therefore, the control section 600 executing the anomaly determination process can determine the wire-breakage anomaly state of the corona core wire 202 based on the secondary-side current $(I_{dc}+I_{trp}+I_c)$.

In the case where the corona core wire 202 is in the wire-breakage anomaly state, the ion electric power generated at the secondary coil of the first isolation transformer 720*a* can be supplied to a region extending from the secondary coil to the breakage point of the corona core wire 202, but cannot be supplied to a region extending from the breakage point of the corona core wire 202 to the ion generation section 110. Namely, in the case where the corona core wire 202 is in the wire-breakage anomaly state, no ions are generated at the ion generation section 110, and movement of ions from the ion generation section 110 to the ion trapping section 130 does not occur. Therefore, no current flows to the first ion current path 233 due to ions trapped by the ion trapping section 130.

Therefore, it is possible to determine whether or not the corona core wire 202 is in the wire-breakage anomaly state; i.e., the corona core wire 202 is broken, by comparing the corona low side current C1 which is the secondary-side current $(I_{dc}+I_{trp}+I_c)$ and the current determination value C1*min* and determining whether or not the corona low side current C1 is equal to or smaller than the current determination value C1*min*.

In the case where the control section 600 has proceeded to S140 as a result of the affirmative determination in S130, in S140, the control section 600 increments (adds 1 to) the wire-breakage anomaly counter CNB.

In the case where the control section 600 has proceeded to S150 as a result of the negative determination in S130, in S150, the control section 600 resets the wire-breakage anomaly counter CNB (CNB=0). After completing the process of S150, the control section 600 again proceeds to S120.

After completing the process of S140, the control section 600 proceeds S160. In S160, the control section 600 determines whether or not the number of times counted by the wire-breakage anomaly counter CNB is equal to or greater than a predetermined wire-breakage determination threshold Cth (for example, Cth=1000 [times]). When the control section 600 makes an affirmative determination (Yes), the control section 600 proceeds to S170, and when the control section 600 makes a negative determination (No), the control section 600 proceeds to S120.

In the case where the control section 600 has proceeded to S170 as a result of the affirmative determination in S160, in S170, the control section 600 determines that the wire-breakage anomaly of the corona core wire 202 has occurred in the particulate sensor 100 and executes, as a notifying process (informing process), a process of notifying (informing) that anomalous state. In S170, the control section 600 executes a process of displaying on the informing section 920 an anomaly informing image showing the wire-breakage anomaly of the corona core wire 202.

In the anomaly determination process, the control section 600 repeatedly executes the processes of the above-described steps S120 to S160 until it makes an affirmative determination in S160.

Notably, in the anomaly determination process, the period between a point in time when S160 is executed one time and a point in time when S160 is executed again (in other word, the execution interval of S160) is set to 10 msec, and in S160, the control section 600 determines whether or not the wire-breakage anomaly of the corona core wire 202 has continued for 10 sec (=10 msec×Cth (=1000 times)) or longer.

Namely, in the anomaly determination process, when the control section 600 determines that the wire-breakage anomaly of the corona core wire 202 has continued for 10 sec or longer (an affirmative determination in S160), the control section 600 determines that the wire-breakages anomaly has occurred and executes a process for notifying (informing) that anomalous state (S170).

[1-7. Effects]

As described above, the particulate measurement apparatus 300 in the particulate measurement system 10 of the present embodiment is configured such that the anomaly determination process is executed in the control section 600.

In the particulate measurement apparatus 300, when an anomaly of the electrical connection state has occurred at the corona cable 201 (specifically, the corona core wire 202), at the ion generation section 110 (specifically, the first electrode 112), etc., the supply of electric power from the first isolation transformer 720*a* (specifically, its secondary coil) to the ion generation section 110 (the first electrode 112) is not performed properly. Notably, an example of the anomaly of the electrical connection state is the wire-breakage anomaly of the corona core wire 202.

In this case, since the ion generation section 110 cannot generate ions properly, the generation of electrified particulates at the electrification chamber 121 cannot be performed properly, and the trapping of ions at the ion trapping section 130 cannot be performed properly. Therefore, the current flowing from the ion trapping section 130 to the first ion current path 233 through the corona inner conductor 204 exhibits an anomalous behavior different from that in the case where the electrical connection state is normal. As a result, the secondary-side current which flows between the secondary-side ground SGL and the point 233*b* on the first ion current path 233 to which the compensation current $I_c$ is supplied (in other word, the secondary-side current ($I_{dc}+I_{trp}+I_c$) flowing through the shunt resistor 230) also exhibits an anomalous behavior different from that in the case where the electrical connection state is normal.

Therefore, the control section 600 can determine whether or not the corona core wire 202 is in the wire-breakage anomaly state; i.e., the corona core wire 202 is broken, based on the corona low side current C1 which is the secondary-side current ($I_{dc}+I_{trp}+I_c$).

As a result, the particulate measurement apparatus 300 can determine the anomaly (wire-breakage anomaly) of the electrical connection state at the corona cable 201, the ion generation section 110, etc., without directly detecting the voltage at the corona cable 201 or the ion generation section 110.

Specifically, the control section 600 determines whether or not the corona low side current C1 is equal to or smaller than the current determination value C1*min* and determines whether or not the corona core wire 202 is in the wire-breakage anomaly state; i.e., the corona core wire 202 is broken, based on the determination result.

As described above, in the case where the corona core wire 202 is in the wire-breakage anomaly state, the ion current measurement circuit 740 enters a state in which it does not supply the compensation current $I_c$ to the first ion current path 233, and the secondary-side current ($I_{dc}+I_{trp}+I_c$) flowing through the shunt resistor 230 of the first ion current path 233 decreases.

Therefore, it is possible to determine whether or not the corona core wire 202 is in the wire-breakage anomaly state; i.e., the corona core wire 202 is broken, by comparing the corona low side current C1 which is the secondary-side current ($I_{dc}+I_{trp}+I_c$) and the current determination value C1*min*, and determining whether or not the corona low side current C1 is equal to or smaller than the current determination value C1*min*.

The control section 600 determines whether or not the corona low side current C1 is equal to or smaller than the current determination value C1*min* in the anomaly determination process (S130). When the corona low side current C1 is equal to or smaller than the current determination value C1*min*, the control section 600 provisionally determines that the corona core wire 202 is in the wire-breakage anomaly state; i.e., the corona core wire 202 is broken, and increments the wire-breakage anomaly counter CNB (S140).

When the count value of the wire-breakage anomaly counter CNB is equal to or greater than the wire-breakage determination threshold Cth (affirmative determination in S160), the control section 600 determines that the corona core wire 202 is in the wire-breakage anomaly state (S170).

Namely, the control section 600 does not immediately determine that the corona core wire 202 is in the wire-breakage anomaly state when the corona low side current C1 becomes equal to or smaller than the current determination value C1*min*. Instead, the control section 600 determines that the corona core wire 202 is in the wire-breakage anomaly state when the state in which the corona low side current C1 is equal to or smaller than the current determination value C1min continues for a wire-breakage anomaly time (10 sec in the present embodiment) or longer (S170). The wire-breakage anomaly time is determined in advance based on the execution interval of S160 and the wire-breakage determination threshold Cth.

By performing the anomaly determination in the above-described manner, the control section 600 does not erroneously determine that the corona core wire 202 is in the wire-breakage anomaly state in the case where the corona low side current C1 temporarily becomes equal to or smaller than the current determination value C1min due to the influence of noise or the like.

Therefore, in the particulate measurement apparatus 300, since the frequency of occurrence of erroneous determination due to the influence of noise or like can be decreased, the determination accuracy in determining the wire-breakage anomaly state of the corona core wire 202 can be improved.

When the control section 600 makes an affirmative determination in S160 of the anomaly determination process, the control section 600 determines that the wire-breakage anomaly of the corona core wire 202 has occurred and executes a process of notifying (informing) that anomalous state (S170). Namely, as the notifying process (informing process), the control section 600 executes a process of displaying on the informing section 920 an anomaly informing image showing the wire-breakage anomaly of the corona core wire 202.

The particulate measurement apparatus 300 including such a control section 600 can inform a user of the particulate measurement apparatus 300 of the wire-breakage anomaly state of the corona core wire 202 through the informing section 920, to thereby prompt the user of the particulate measurement apparatus 300 to check the connection state of the corona cable 201 or to exchange the corona cable 201.

As a result, the particulate measurement apparatus 300 can prevent the particulate measurement using the particulate sensor 100 from being continued in a situation in which the corona core wire 202 is in the wire-breakage anomaly state, to thereby prevent lowering of the measurement performance of the particulate sensor 100.

The particulate measurement system 10, which is configured by connecting the particulate sensor 100 to the above-described particulate measurement apparatus 300 through the corona cable 201, can determine the anomaly of the electrical connection state at the corona cable 201 (the corona core wire 202), the ion generation section 110 (the first electrode 112), etc., without directly detecting the voltage at the corona cable 201 (specifically, the corona core wire 202) or the ion generation section 110 (specifically, the first electrode 112).

[1-8. Corresponding Structure]

Next, structure corresponding to terms used herein to define the invention include the following.

The particulate measurement system 10 corresponds to an example of the particulate measurement system; the particulate measurement apparatus 300 corresponds to an example of the particulate measurement apparatus; the particulate sensor 100 corresponds to an example of the particulate sensor; the corona cable 201 corresponds to an example of the corona cable; and the informing section 920 corresponds to an example of the informing section.

The first isolation transformer 720a corresponds to an example of the isolation transformer for corona discharge; the first ion current path 233 and the second ion current path 237 correspond to an example of the signal line; the primary-side ground PGL corresponds to an example of the primary-side potential; the secondary-side ground SGL corresponds to an example of the secondary-side potential; the control section 600 and the ion current measurement circuit 740 correspond to an example of the particulate computation section; the control section 600 and the corona current measurement circuit 730 correspond to an example of the corona discharge control section; and the control section 600 executing the anomaly determination process corresponds to an example of the anomaly determination section.

The ion generation section 110 corresponds to an example of the ion generation section; the electrification chamber 121 corresponds to an example of the electrification chamber; the ion trapping section 130 corresponds to an example of the trapping section; and the metallic support 140 corresponds to an example of the metallic support. The corona core wire 202 corresponds to an example of the corona core wire; the corona inner conductor 204 corresponds to an example of the inner shield wire; and the corona outer conductor 203 corresponds to an example of the outer shield wire.

2. Other Embodiments

An embodiment of the present invention has been described; however, the present invention is not limited to the above-described embodiment and can be implemented in various forms without departing from the gist of the invention.

The numerical value of the current determination value C1min is not limited to the above-described numerical value, and an appropriate value may be set in accordance with application or environment of use. In other words, the determination value for the corona low side current C1 (the secondary-side current ($I_{dc}+I_{trp}+I_c$)) in S130 is not limited to 2 µA, and a proper value may be set in accordance with application or environment of use.

Also, the numerical value of the wire-breakage determination threshold Cth is not limited to the above-described numerical value, and an appropriate value may be set in accordance with application or environment of use. In other words, the determination value for the continuation time of the anomalous state in S160 is not limited to 10 sec (=10 msec×Cth (=1000 times)), and may be set to 5 sec, 20 sec, etc., in accordance with application or environment of use.

The informing section 920 is not limited to the display unit, and may be a sound output unit which outputs an anomaly informing sound informing the wire-breakage anomaly of the corona core wire. Alternatively, the informing section may include both the display unit and the sound output unit.

Also, in the above-described embodiment, the particulate sensor 100 includes the second electrode 132. However, the particulate sensor may be configured without use of the second electrode 132. Even when the second electrode 132 is omitted, the amount of particulates can be measured based on the amount of electrified particulates, and the structure of the particulate sensor can be simplified to a degree corresponding to the omission of the second electrode 132. In such a case, the second power supply circuit 710b, the second isolation transformer 720b, the second rectification circuit 752, the short protection resistor 754, and the auxiliary current path 235 may be omitted from the electric circuit section 700.

Also, the structure of the particulate sensor which constitutes the particulate measurement system is not limited to the structure in which the ion generation section is disposed in line outside the exhaust gas electrification section. For example, a structure can be employed in which the ion generation section is disposed inside the exhaust gas electrification section. Further, in the case where the particulate sensor constituting the particulate measurement system is configured such that the ion generation section is disposed inside the exhaust gas electrification section, the air supply section may be omitted from the particulate measurement apparatus. Further, the particulate sensor may have a structure in which the supply of high-pressure air to the electrification chamber by the air supply section is not performed. For example, such a particulate sensor may have a sensor structure such as that disclosed in US 2015/0192545 published on Jul. 9, 2015 (corresponding to Japanese Patent Application Laid-Open (kokai) No. 2015-129711) by the present applicant, the disclosure of which is incorporated herein by reference in its entirety.

Also, the corona current measurement circuit is not limited to the optical-coupling-type isolation amplifier and may be, for example, a magnetic-coupling-type or capacitive-coupling-type isolation amplifier.

Further, the corona cable is not limited to the triaxial cable (a cable in which the corona core wire, the corona inner conductor, and the corona outer conductor are coaxially disposed in this order from the inner side toward the outer side). For example, a cable in which the corona core wire, the corona inner conductor, the corona outer conductor are disposed in parallel, and the corona inner conductor and the corona outer conductor do not cover the corona core wire may be used as the corona cable. Alternatively, a cable which is composed of a first cable including the corona core wire and the corona inner conductor and a second cable including the corona outer conductor and in which the first cable and the second cable can be separated from each other may be used as the corona cable.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2016-191373 filed Sep. 29, 2016, incorporated herein by reference in its entirety.

What is claimed is:

1. A particulate measurement apparatus for electrical connection to a particulate sensor for detecting particulates contained in a gas under measurement and which controls the particulate sensor so as to measure the amount of the particulates contained in the gas under measurement,
   wherein the particulate sensor comprises:
   an ion generation section for generating ions by means of corona discharge;
   an electrification chamber into which the gas under measurement is introduced and which electrifies the particulates contained in the gas under measurement by mixing with the ions generated by the ion generation section to thereby produce electrified particulates;
   a trapping section which traps the ions generated by the ion generation section but not used for the electrification of the particulates; and
   a metal support which supports the ion generation section, the electrification chamber, and the trapping section in a condition in which the metal support is electrically insulated from the ion generation section, the electrification chamber, and the trapping section,
   wherein the particulate measurement apparatus comprises:
   an isolation transformer for corona discharge which has a primary coil and a secondary coil and which performs voltage conversion;
   a signal line which forms at least a portion of a signal path extending from the trapping section to a line of a secondary-side reference potential which is a reference potential of the secondary coil;
   a particulate computation section which computes the amount of the particulates contained in the gas under measurement based on a current value of compensation current supplied to the signal line in accordance with the amount of the electrified particulates discharged from the particulate sensor; and
   a corona discharge control section which controls the amount of electric power supplied to the primary coil, based on a secondary-side current flowing through the signal path, so as to control ion electric power generated at the secondary coil,
   the particulate measurement apparatus being electrically connected to the particulate sensor through a corona cable which includes a corona core wire, an inner shield wire, and an outer shield wire,
   the corona core wire forming at least a portion of a path for supplying electric power from the secondary coil to the ion generation section,
   the inner shield wire being electrically insulated from the corona core wire and being electrically connected to the trapping section and the signal line,
   the outer shield wire being electrically insulated from the corona core wire and the inner shield wire and being electrically connected to the metal support and a line of a primary-side reference potential which is a reference potential of the primary coil,
   wherein the particulate measurement apparatus further comprises an anomaly determination section which determines, based on the secondary-side current, whether or not the corona core wire is in a wire-breakage anomaly state in which the corona core wire is broken.

2. The particulate measurement apparatus as claimed in claim 1, wherein the anomaly determination section determines that the corona core wire is in the wire-breakage anomaly state when the secondary-side current is equal to or smaller than a predetermined determination value.

3. The particulate measurement apparatus as claimed in claim 2, wherein the anomaly determination section determines that the corona core wire is in the wire-breakage anomaly state when the state in which the secondary-side current is equal to or smaller than the determination value continues for a predetermined wire-breakage anomaly time or longer.

4. The particulate measurement apparatus as claimed in claim 1, further comprising an informing section which informs that the corona core wire is in the wire-breakage anomaly state in the case where the anomaly determination section determines that the corona core wire is in the wire-breakage anomaly state.

5. A particulate measurement system comprising:
a particulate sensor for detecting particulates contained in a gas under measurement; and
the particulate measurement apparatus as claimed in claim 1 which is electrically connected to the particulate sensor through the corona cable and which controls the particulate sensor so as to measure the amount of the particulates contained in the gas under measurement.

* * * * *